United States Patent

Milkowski et al.

Patent Number: 4,595,531
Date of Patent: Jun. 17, 1986

[54] PROCESS OF MAKING BENZODIAZEPINE DERIVATIVES

[75] Inventors: Wolfgang Milkowski, Burgdorf; Renke Budden, Peine; Siegfried Funke, Hanover; Rolf Hüschens, Laatzen; Hans-Günther Liepmann, Hanover; Werner Stühmer, Eldagsen; Horst Zeugner, Hanover, all of Fed. Rep. of Germany

[73] Assignee: Kali-Chemie AG, Hanover, Fed. Rep. of Germany

[21] Appl. No.: 602,279

[22] Filed: Apr. 24, 1984

Related U.S. Application Data

[63] Continuation of Ser. No. 598,880, Jul. 24, 1975, abandoned, which is a continuation-in-part of Ser. No. 359,989, May 1, 1973, abandoned.

[30] Foreign Application Priority Data

May 3, 1972 [DE] Fed. Rep. of Germany ....... 2215583

[51] Int. Cl.[4] .................. C07D 243/14; C07D 401/06; C07D 403/06; C07D 413/06
[52] U.S. Cl. .......................... 260/239 BD; 260/243.3; 260/244.4; 260/245.7; 564/166; 564/176; 564/185; 564/368
[58] Field of Search .......... 260/239 BD, 243.3, 244.4, 260/245.7

[56] References Cited

FOREIGN PATENT DOCUMENTS 2221558 11/1973 Fed. Rep. of Germany ...... 260/239

*Primary Examiner*—Alton D. Rollins
*Attorney, Agent, or Firm*—Schwartz, Jeffery, Schwaab, Mack, Blumenthal & Evans

[57] ABSTRACT

Benzodiazocines corresponding to the formula

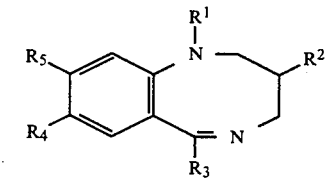

are converted to benzodiazepines corresponding to the formula

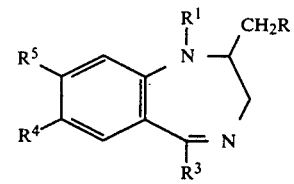

of claim 1 by subjecting the benzodiazocine (a) if it is halogen-substituted in the 3-position to a thermal treatment which may also take place in the presence of a nucleophilic agent for the reaction or (b) if the 3-position is hydroxy substituted to treatment with a Lewis acid which is a chlorinating or brominating agent. Whenever the diazepine obtained as the final product has a 2-halogenomethyl group it may then be converted to benzodiazepine which is otherwise substituted in the 2-position.

20 Claims, No Drawings

PROCESS OF MAKING BENZODIAZEPINE DERIVATIVES

CROSS-REFERENCE TO RELATED CASES

This application is a continuation of application Ser. No. 598,880, filed July 24, 1975, abandoned, which is a continuation in part of application Ser. No. 359,989 filed May 1, 1973, now abandoned. The benzodiazepines obtained are further shown and specified in our application 355,986, filed May 1, 1973 now Pat. No. 3,998,809. The benzodiazocines used as starting products are further shown and discussed in our application Ser. No. 871,741, now U.S. Pat. No. 4,243,585, which is a continuation of our application Ser. No. 588,969 filed June 20, 1975, abandoned, which is a continuation in part of Ser. No. 355,987, filed May 3, 1973, now abandoned.

1,4-Benzodiazepines have been disclosed in the literature as valuable pharmaceutical compounds, see Burger, Medicinal Chemistry (1970), part 2, third edition.

However, the 1,4-Benzodiazepines corresponding to the formula

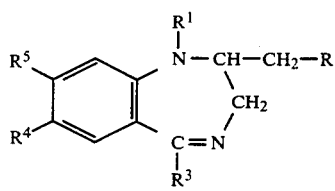

wherein R is halogen, hydroxy, an alkylcarbonyloxy or benzoyloxy, alkoxy, phenoxy, halophenoxy, thiophenoxy, cyano, amino, benzylamino, monoalkylamino, dialkylamino, phthalimido, morpholino, piperidino or N-methylpiperazino, wherein the alkylcarbonyloxy, alkoxy, and alkyl groups contain at most 6 carbon atoms in the alkyl portion;

$R^1$ is hydrogen, 2-halogenoethyl, 2-methoxyethyl, benzyl or alkyl having at most 6 carbon atoms;

$R^3$ is phenyl, halophenyl, lower alkylphenyl, nitrophenyl, trifluoromethylphenyl, dihalophenyl, dimethoxyphenyl or trimethoxyphenyl;

$R^4$ is hydrogen, chloro, fluoro, bromo, nitro, trifluoromethyl, methyl, methoxy or methylthio;

$R^5$ is hydrogen or methoxy; or $R^4$ and $R^5$ together may form ethylenedioxy; or a pharmaceutically acceptable acid addition salt thereof, to applicants' knowledge, have nowhere been disclosed so far.

Lower alkyl in these compounds identified by $R_1$ may for instance be methyl, ethyl, propyl, isopropyl, butyl, sec.-butyl, tert.-butyl, amyl, hexyl. $R_1$ may also be cyclopentyl, cyclohexyl or cyclopropylmethyl. $R_1$ can also be an aromatic substituted alkyl residue or an alkyl residue which is substituted with a halogen, a free esterified or etherified hydroxyl group.

UTILITY AND TESTS

The compounds of the invention are in particular useful in their action on the central nervous system. They have an anticonvulsive, sedative, muscle relaxant and tranquilizer effect.

They can be used with the usual pharmaceutically acceptable diluents or carrier materials such as cellulose, starch, polyethylene glycol, magnesium stearate or talcum. Water-soluble compounds can also be administered as aqueous solutions.

The dosage depends on age, body weight and condition of the patient. Preferred is a dose of 1 to 200 mg per day per kg of body weight. The amount may be administered as a single dose per day or may be spread throughout the day. Normally smaller doses are used in case of parenteral administration.

The main use of the compounds is as tranquilizers with only small musculotropic properties in the treatment of mental afflictions. They can be administered per os or parenterally to human patients and animals.

The following tests have been carried out with animals. The compounds are particularly distinguished by their excellent compatibility (therapeutic index) when compared with the normal commercial products.

The tests were carried out to determine the following action of the compounds.

[1] TESTS REGARDING ANTICONVULSIVE ACTIVITY (a) Electroshock attacks

The test substances as appearing from the Table further below were administered per os to groups of five mice each at a logarithmic dosage spacing of 0.1673 (Hakkenberg, U. and H. Bartling, Naunyn-Schmiedeberg's Arch. exp. Path. u. Pharmak. 235, 437–468 (1959). One hour after application the electrodes were attached to the ears of the animals and the electrical shock or stimulus was applied. The appearance or absence of tonic extenser attacks was recorded and the percentage of protective action against the attacks was determined.

(b) Pentetrazole spasm

The test substances as listed below were applied to groups of 10 mice each per os and likewise at a logarithmic spacing of the dosage by 0.1673. Sixty minutes after application pentetrazole (pentylenetetrazole) was injected subcutaneously at a dosage of 100 mg/kg. The appearance of clonic and tonic convulsions and death was observed during a time of 45 minutes. The total observation time was up to 3 hours. The protective effect against convulsion and death was determined by comparison in simultaneously performed tests with control animals. The effective dose $ED_{50}$ against convulsions was determined from the probability logarithmic dosage curves.

[2] TEST REGARDING ANTIAGGRESSIVE ACTION IN AN ELECTRICALLY IRRITATED FIGHTER MOUSE

The method is described in Tedeschi, R. E. et al. J. Pharmacol. Exptl. Therap. 125, 28 (1959). One hour after application per os of the test compounds eight pairs of mice per dose were tested by the mentioned method regarding the aggression properties. The logarithmic dosage spacing was likewise 0.1673. The time of the stimulation was 3 minutes.

[3] TEST REGARDING ANESTHESIA POTENTIATING PROPERTIES AFTER APPLICATION OF HEXOBARBITAL

The method involved again the administration of the test substances at a logarithmic dose spacing per os of 0.3324. Thirty minutes after application hexobarbital was applied at a dose of 65 mg/kg by intravenous application. The duration of the sleeping time was determined. $ED_{50}$ was taken as equal to 30 minutes in sideposition.

[4] ACUTE TOXICITY

The acute toxicity was determined after a single application per os in white NMRI mice which had not been fed. The calculation was effected by the method of Litchfield, J. T. and F. Wilcoxon (J. Pharmacol. Exptl. Therap. 96 99 (1949).

The test results appear from the following Table.

TABLE 1

| TESTS REGARDING ACTIVITY (all amounts in mg/kg) | $LD_{50}$ per os | Electroshock p.o. $ED_{50}$ | Pentetrazole-spasm p.o. $ED_{50}$ | Fighter mouse p.o. $ED_{50}$ | Anaesthesia p.o. $ED_{50}$ |
|---|---|---|---|---|---|
| 7-chloro-1-methyl-2-methoxymethyl-5-(2-chlorophenyl)-2,3-dihydro-1H—1,4-benzodiazepine hydrochloride | >1470 | 46 | 2,2 | 45 | 1,6 |
| 7-chloro-1-methyl-2-hydroxymethyl-5-(2-chlorophenyl)-2,3-dihydro-1H—1,4-benzodiazepine | 4640 | 46,4 | 13,2 | 46 | 2,0 |

MAKING OF STARTING MATERIALS

The compounds of the invention of formula I are made by starting from acyldiamines of the formula

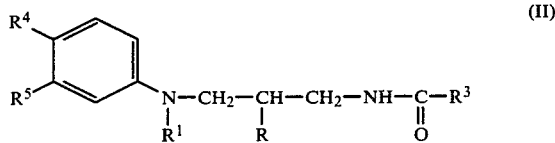
(II)

wherein $R^1$, $R^3$, $R^4$ and $R^5$ have the same meaning as given above in connection with formula I and wherein R is a free or esterified hydroxyl group.

These compounds are themselves novel. They can be made by reacting a diamine of the formula

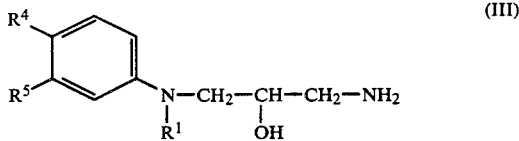
(III)

in which $R^1$, $R^4$ and $R^5$ have the meaning as just given with a carboxylic acid derivative in a suitable solvent which acid derivative should be adapted to form carboxylic acid amides and -esters. As carboxylic acid derivatives of this type can particularly be used carboxyl acid esters, carboxylic acid anhydrides, mixed carboxylic acid anhydrides and carboxylic acid halides.

The reaction can be carried out in an inert solvent in the presence of an acid acceptor (acid binding reagent). As such there are particularly suitable tertiary amines, such as, triethylamine or pyridine. If the acid binding reagent is used in an excess it can also be employed as the solvent for the reaction. The reaction can however also be carried out in the absence of an acid binding reagent by using an inert solvent. Such inert solvents are for instance methylenechloride, chloroform, acetone, dioxane, benzene, toluene, chlorobenzene, etc. The temperature of the reaction is determined by the type of carboxylic acid derivative and is between −30° C. and the boiling point of the particular solvent. The reaction can be carried out at atmospheric pressure but also at an elevated pressure.

If the reaction is carried out by using equimolar amounts there are in preference obtained amides of the above formula II wherein R is OH. The hydroxyl group in these compounds can, if desired, be esterified with suitable carboxylic acid derivatives, such as, carboxylic acid anhydrides, -esters or -chlorides. Upon use of two mols of the particular carboxylic acid derivative per mol of diamine an esterification of the hydroxyl group occours simultaneously with the amide formation. If compounds of the formula III above in which $R_1=H$ are reacted with three mols of a suitable carboxylic acid derivative, triacyl derivatives are obtained.

In application Ser. No. 355,986 filed on May 1, 1973, now U.S. Pat. No. 3,998,809, the inventors have disclosed another process for making the benzodiazepine compounds by direct cyclization of the above acyldiamines of formula II. The present application relates to the process of making the benzodiazepines via benzodiazocines as intermediates.

In our copending patent application No. Ser. No. 588,969 filed June 20, 1975, continuation in part of Ser. No. 355,987 filed on May 3, 1973 the benzodiazocine compounds themselves are disclosed and claimed. They are made by subjecting an acyldiamine of the formula II above given to cyclization at elevated temperature in an inert solvent with a phosphorus oxyhalide, preferably phosphorus oxychloride, under conditions to obtain the intermediate benzodiazocines having the following formula:

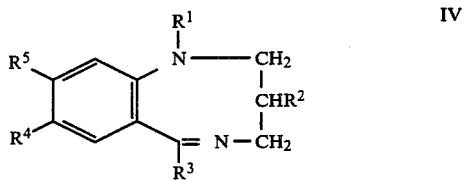
IV in which $R^1$, $R^3$, $R^4$ and $R^5$ have the meaning as above indicated and $R^2$ is halogen, or acetyloxy or benzoyloxy. If it is desired to obtain a compound in which $R^2$ is hydroxy the first obtained acyloxy compound of formula IV is converted with a hydrolyzing agent to the compound wherein $R^2$ is hydroxy. The ring closure reaction with the cyclization agent must be carried out at conditions where a ring closure occurs so as to obtain the benzodiazocine compound. In cases where R in the acyldiamine used as starting product is hydroxy the preferred cyclization agent is phosphorus oxychloride. An inert solvent may be used for instance chlorobenzene or an excess of the cyclization agent.

The reaction is preferably carried out at a temperature between 50° and 100° C. since at higher temperatures the formation of byproducts occurs with ring contraction.

The temperature also depends on the substituents in phenyl rings in the amides of formula II. E.g., if $R^5$ is an alkoxy radical a lower cyclization temperature can be used as if a hydrogen atom is present in that same position.

The cyclization reaction is accomplished by the exchange of hydroxyl for halogen. Thus the ring compound obtained is a 3-halogenobenzodiazocine. The halogenoacyldiamines obtained as intermediates in the reaction of acyldiamines where R is hydroxy with a phosphorus oxyhalide may be isolated in the initial reaction.

Where R in the acyldiamine of formula II which is used as starting product is hydroxy it is also possible to protect the hydroxy group prior to the cyclization reaction by converting it to an acetoxy or benzoyloxy group. This has the advantage that the formation of byproducts upon ring contraction is prevented and only the 8-membered benzodiazocines are obtained. The cyclization with phosphorus oxychloride in that case can be effected within a broader temperature range of 50° to 150° C., preferably between 110° and 130° C.

The inert solvents in that case may be nitrobenzene, tetrachloroethane or an excess of the cyclization agent. There are then obtained 3-acyloxy compounds which can be converted in conventional manner into the 3-hydroxy derivatives.

PRESENT PROCESS

In the present application the thus obtained diazocines (compounds IV), are used as the intermediate products for the preparation of the novel pharmacological effective benzodiazepine derivatives of formula I. Surprisingly it has been found that the halogen and hydroxy compounds can be converted in good yields by ring contraction and molecular rearrangement to the benzodiazepine derivatives of formula I which are substituted in the 2-position.

The halogen compound IV i.e. the diazocine in which $R^2$ is halogen, can be subjected in an inert solvent to a thermal treatment, e.g. by reflux temperature of the solvent, preferably at temperatures higher than 100° C. The inert solvents may be e.g. nitrobenzene or tetrachloroethane. In this case, the 2-halomethylbenzodiazepine derivative of formula I is obtained which can be converted to the other derivatives of the formula I, if desired, by replacement of the halogen atom by reaction with a nucleophilic agent by methods already known in the art. Thus the 2-halomethylbenzodiazepines can be directly reacted with amines, anions of amides, anions of imides, alcoholates, phenolates, cyanides, thioalcoholates, thiophenolates or anions of alkylcarboxylic acids or benzoic acids, possibly in the presence of an inert solvent and at elevated temperature. Alternatively, these compounds can be obtained via a reactive intermediate. The 2-hydroxymethylbenzodiazepines can be obtained by alkaline hydrolysis.

The aforementioned halogen compounds IV can also be subjected to the thermic treatment under suitable conditions in an inert solvent with a nucleophilic reagent. In this case a large number of pharmaceutically interesting benzodiazepine derivatives of the formula I can be directly obtained according to the reaction.

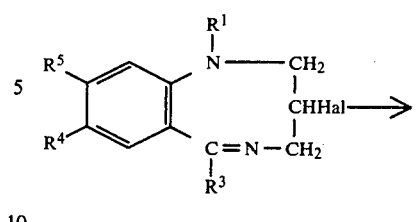

IV

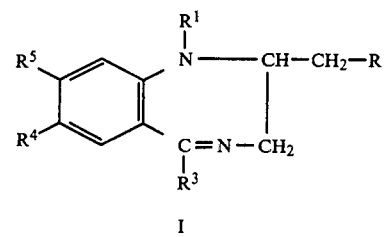

I

By the employment of a nucleophilic agent being a member of the group: alkali hydroxide, anions of alkyl carboxylic acids or benzoic acid, alcoholate, the alkyl moieties have at most 6 carbon atoms, phenolate, halophenolate, thiophenolate, cyanide, ammonia, benzylamino, monoalkylamino or dialkylamino, the alkyl moieties have at most 6 carbon atoms, anion of phthalimide, morpholino, piperidino or N-methylpiperazino, the radical R may be a hydroxy group, an alkyl carbonyloxy or benzoyloxy, alkoxy, the alkyl moieties have at most 6 C-atoms, phenoxy, halophenoxy, thiophenoxy, cyano, amino, benzylamino, monoalkylamino or dialkylamino, the alkyl moieties have at most 6 carbon atoms, phthalimido, morpholino, piperidino or N-methylpiperazino radicals.

Surprisingly the molecular rearrangement and contraction of the ring of the benzodiazocine derivative of formula IV whereby the diazepine is formed proceeds in good yields irrespective of the particular nucleophilic reagent that has been chosen. The reaction is conveniently performed at elevated temperature, e.g. by reflux temperature, in an inert solvent and possibly the nucleophilic reagent itself may serve as the solvent.

The 3-hydroxy benzodiazocines of formula IV $R^2$=hydroxy can also be treated with Lewis acids, particularly those acting also as halogenating agents, such as phosphorus trihalide, phosphorus oxyhalide, preferably thionylchloride. The compound can thus be converted into 2-halogenomethyl benzodiazepines of formula I. The reaction can be carried out in a solvent and elevated temperature.

Acids suitable for making the non-toxic addition salts of compounds I are e.g., acetic, propionic, diethylacetic, malonic, fumaric, maleic, lactic, tartaric, citric, sulphoric, hydrobromic or orthophosphoric acid. These acid-addition salts can be used for pharmaceutical purposes like the free bases and have the advantage to be water-soluble.

EXAMPLES SHOWING MAKING OF STARTING PRODUCTS

The following examples illustrate the making of the acyldiamines of the above formula II by starting from a diamine of above formula III.

EXAMPLE 1

A solution of 128 g N-methyl-N-(2-hydroxy-3-aminopropyl)-4'-chloroaniline in 200 ml chloroform was successively reacted with 84 ml triethylamine and 69.5 ml of benzoylchloride. The chloroform solution was washed with water after 24 hours and dried. The chloroform was then distilled off in a vacuum and the crude product was subjected to recrystallization from benzene. There were obtained 142,5 g-N-methyl-N-(2-hydroxy-3-benzoylaminopropyl)-4'-chloroaniline; m.p. 136° to 137° C.

EXAMPLE 2

A solution of 59 g of N-methyl-N-(2-hydroxy-3-aminopropyl)-4'-chloroaniline in 1 liter chloroform was successively reached with 85 ml of triethylamine and 70 ml of benzoylchloride. The mixture was then heated under reflux for 4 hours and further processed as described below in Example 3. The crude product was recrystallized from isopropanol. There were obtained 61 g of N-methyl-N-(2-benzoyloxy-3-benzoylaminopropyl)-4'-chloroaniline; m.p. 145° to 148° C.

EXAMPLE 3

A solution of 45,4 g of N-methyl-N-[2-hydroxy-3-(3',4',5'-trimethoxybenzoyl)-aminopropyl]-aniline in 250 ml pyridine was reacted with 250 ml of acidic acid anhydride. The solution was poured into water after 48 hours and extracted with chloroform. The chloroform solution was concentrated by evaporation in a vacuum and the residue was recrystallized from ether. There was obtained N-methyl-N-[2-acetoxy-3-(3',4',5'-trimethoxybenzoyl)-aminopropyl]-aniline; m.p. 90° to 92° C.

In the same manner as just described in Examples 1 to 3 the following compounds were made.

N-methyl-N-[2-hydroxy-3-(3',4'-dimethoxybenzoyl)-aminopropyl]-3',4'-diimethoxyaniline, (oil);
N-methyl-N-[2-hydroxy-3-(3',4'-dimethoxybenzoyl)-aminopropyl]-3',4'-ethylenedioxyaniline, (oil);
N-methyl-N-[hydroxy-3-(2'-chlorobenzoyl)-aminopropyl]-3',4'-ethylenedioxyaniline, m.p. 105°–107° C.;
N-methyl-N-(2-hydroxy-3-benzoylaminopropyl)-4'-methylthioanilin, m.p. 141°–142° C.;
N-methyl-N-[2-hydroxy-3-(2',6'-dichlorobenzoyl)-aminopropyl]-4'-chloroaniline, (oil);
N-methyl-N-[2-hydroxy-3-(2',3'-dichlorobenzoyl)-aminopropyl]-4'-chloroaniline, m.p. 91°–95° C.;
N-methyl-N-[2-hydroxy-3-(2'-methylbenzoyl)-aminopropyl]4'-chloroaniline, m.p. 108°–113° C.;
N-methyl-N-[2-hydroxy-3-(2'bromobenzoyl)-aminopropyl]4'-chloroaniline, m.p. 118°–123° C.;
N-methyl-N-[2-hydroxy-3-(2'-nitrobenzoyl)-aminopropyl]4'-chloroaniline, m.p. 132°–133° C.;
N-ethyl-N-(2-hydroxy-3-benzoylaminopropyl)-4'-chloroaniline, m.p. 121°–123° C.;
N-β-methoxyethyl-N-(2-hydroxy-3-benzoylaminopropyl)-4'-chloroaniline, m.p. 120°–122° C.;
N-methyl-N-[2-hydroxy-3-(3',4',5'-trimethoxybenzoyl)-aminopropyl]-aniline, m.p. 126°–129° C.;
N-methyl-N-(2-hydroxy-3-benzoylaminopropyl)-4'-fluoroaniline, m.p. 115°–118° C.;
N-methyl-N-[2-hydroxy-3-(2'-fluorobenzoyl)-aminopropyl]-4'-chloroaniline, m.p. 105°–107° C.;
N-methyl-N-(2-hydroxy-3-benzoylaminopropyl)-aniline, m.p. 100°–103° C.;
N-(2-hydroxy-3-benzoylaminopropyl)-4'-chloroanilin, m.p. 175°–177° C.;
N-cyclopropylmethyl-N-(2-hydroxy-3-benzoylaminopropyl)-4'-chloroaniline, m.p. 110°–112° C.;
N-methyl-N-(2-acetoxy-3-benzoylaminopropyl)-aniline, (oil);
N-methyl-N-[2-acetoxy-3-(2'-fluorobenzoyl)-aminopropyl]-4'-chloroaniline, (oil);
N-methyl-N-[2-hydroxy-3-(2'-chlorobenzoyl)-aminopropyl]-4'-chloroaniline, m.p. 113°–115° C.
N-methyl-N-[2-hydroxy-3-(2'-trifluoromethylbenzoyl)-aminopropyl]-4'-chloroaniline. m.p. 107°–109° C.;
N-methyl-N-[2-hydroxy-3-(3',4'-dimethoxybenzoyl)-aminopropyl]-4'-chloroaniline, m.p. 118°–121° C.;
N-methyl-N-[2-hydroxy-3-(3',4'-dichlorobenzoyl)-aminopropyl]-4'-chloroaniline, m.p. 115°–117° C.;
N-methyl-N-(2-benzoyloxy-3-benzoylaminopropyl)-aniline, m.p. 129°–130° C.
N-methyl-N-[2-hydroxy-3-(2',4'-dichlorobenzoyl)-aminopropyl]-4'-chloroaniline, m.p. 98°–99° C.;
N-methyl-N-(2-hydroxy-3-benzoylaminopropyl)4'-methylaniline, m.p. 115° C.;
N-methyl-N-(2-hydroxy-3-benzoylaminopropyl)-4'-methoxyaniline, m.p. 120° C.;
N-methyl-N-[2-hydroxy-3-(3'-trifluoromethylbenzoyl)-aminopropyl]-4'-chloroaniline, (oil);
N-benzyl-N-(2-hydroxy-3-benzoylaminopropyl)-4'-chloranilin, m.p. 128°–132° C.

MAKING OF THE BENZODIAZOCINE INTERMEDIATES (FORMULA IV)

The following Examples will further illustrate the making of the intermediate diazocine compounds of formula IV.

EXAMPLE 5

61 g of N-methyl-N-(2-benzoyloxy-3-benzoylaminopropyl)-4'-chloroaniline were heated with 60 ml phosphorus oxychloride to 120° C. for 16 hours. The reaction product was then poured on ice, reacted with sodium hydroxide until it was alkaline and extracted with chloroform. The chloroform solution was concentrated by evaporation in a vacuum and the residue was recrystallized from acetone. There was thus obtained 8-chloro-1-methyl-3-benzoyloxy-6-phenyl-1,2,3,4-tetrahydro-1,5-benzodiazocine; m.p. 179° to 180° C.

EXAMPLE 6

5.9 g of the benzodiazocine obtained in Example 5 were heated in 200 ml dioxane with 50 ml of a 5% sodium hydroxide solution under reflux for 20 minutes. The dioxane was then distilled off in a vacuum and the aqueous solution was extracted with chloroform. This was repeated and the various chloroform extracts were then concentrated by evaporation in vacuum and the residue was recrystallized from ether. There was thus obtained 8-chloro-1-methyl-3-hydroxy-6-phenyl-1,2,3,4-tetrahydro-1,5-benzodiazocine; m.p. 169° to 170° C.

EXAMPLE 7

32 g of N-methyl-N-(2-hydroxy-3-benzoylaminopropyl)-4'-chloroaniline were heated with 50 ml phosphorus chloride in 100 ml nitrobenzene to 95° C. during 22 hours. The excess phorphoroxychloride and the nitrobenzene were then distilled off in a vacuum. The residue was taken up in chloroform and treated with ice water and dilute sodium hydroxide as indicated in Example 1. The chloroform solution was concentrated by evaporation in a vacuum. The residue was treated with ether and the ether solution was reacted with an isopropanol solution of hydrogen chloride. After recrystallization from ethanol/ether there was obtained 3,8-dichloro-1-methyl-6-phenyl-1,2,3,4-tetrahydro-1,5-benzodiazocine hydrochloride; m.p. 195° to 196° C.

In the same manner as described in Examples 5 to 7 there were obtained the following compounds:

1-methyl-3-acetoxy-6-phenyl-1,2,3,4-tetrahydro-1,5-benzodiazocine (oil);
1-methyl-3-hydroxy-6-phenyl-1,2,3,4-tetrahydro-1,5-benzodiazocine, m.p. of the maleinate 135°–137° C.;
1-methyl-3-acetoxy-6-(3,4,5-trimethoxyphenyl)-1,2,3,4-tetrahydro-1,5-benzodiazocine, m.p. 191°–192° C.;
1-methyl-3-benzoyloxy-6-phenyl-1,2,3,4-tetrahydro-1,5-benzodiazocine, m.p. 192°–194° C.;
8-chloro-1-methyl-3-hydroxy-6-(2'-chlorophenyl)-1,2,3,4-tetrahydro-1,5-benzodiazocine, m.p. of the hydrochloride 180°–184° C.;
3,8-dichloro-1-methyl-6-(2'-chlorophenyl)-1,2,3,4-tetrahydro-1,5-benzodiazocine, m.p. of the hydrochloride 166°–169° C.

CONVERSION OF THE BENZODIAZOCINES (IV) TO BENZODIAZEPINES (I)

The following Examples will illustrate the conversion of the benzodiazocine compounds of formula IV as above given to the benzodiazepine compounds of formula I.

EXAMPLE 8

100 mg 3,8-dichloro-1-methyl-6-phenyl-1,2,3,4-tetrahydro-1,5-benzodiazocine hydrochloride were heated in 3 ml water and 4 ml dioxane with 0.5 ml of a 20% concentration sodium hydroxide under reflux for a time of 3 hours. The crude product was then extracted with chloroform and the chloroform extracts were concentrated by evaporation in a vacuum. The hydrochloride obtained by reaction of an isopropanol solution thereof with an ether solution of hydrogen chloride was recrystallized from isopropanol. There was thus obtained 7-chloro-1-methyl-2-hydroxymethyl-5-phenyl-2,3-dihydro-1H-1,4-benzodiazepine hydrochloride. This product was the same as obtained in Examples 4 and 7 of application Ser. No. 355 986 by heating N-methyl-N-(2-hydroxy-3-benzoylaminopropyl)-4'-chloranilin with phosphoroxychloride to 120° C. for 40 hours followed by alkalinization and extraction and subsequent reaction with sodium hydroxide in water and dioxane; m.p. 227°–235° C.

EXAMPLE 9

500 mg of 3,8-dichloro-1-methyl-6-phenyl-1,2,3,4-tetrahydro-1,5-benzodiazocine hydrochloride were heated in a solution of 110 mg sodium in 70 ml methanol under reflux for 12 hours. After evaporation of the methanol in a vacuum the mass was further processed with water/chloroform and the chloroform solution was evaporated and concentrated in a vacuum. The residue was taken up in isopropanol and reacted with an ether solution of hydrogen chloride. There was obtained 7-chloro-1-methyl-2-methoxymethyl-5-phenyl-2,3-dihydro-1H-1,4-benzodiazepine hydrochloride which product also was identical with the product obtained directly by reaction of N-methyl-N-(2-hydroxy-3-benzoylaminopropyl)-4'-chloroaniline in phosphoroxychloride at 120° C. and subsequent reaction with sodium and methanol as disclosed in Examples 4 and 8 of application Ser. No. 355 986; m.p. 198°–210° C.

EXAMPLE 10

100 mg of 3,8-dichloro-1-methyl-6-phenyl-1,2,3,4-tetrahydro-1,5-benzodiazocine hydrochloride is heated in 10 ml piperidine under reflux for 24 hours. For processing the mass was poured into water, extracted with chloroform and the chloroform was subsequently distilled off in a vacuum. The product was recrystallized from ether and there was obtained 7-chloro-1-methyl-2-piperidinomethyl-5-phenyl-2,3-dihydro-1H-1,4-benzodiazepine which also was identical with the same material obtained in Examples 4 and 6 of application Ser. No. 355 986 directly by heating acyldiamines with phosphoroxychloride and subsequent reaction with piperidine; m.p. 143°–145° C.

EXAMPLE 11

A solution of 1 g of 8-chloro-1-methyl-3-hydroxy-6-phenyl-1,2,3,4-tetrahydro-1,5-benzodiazocine in 50 ml benzene was heated under reflux for 1 hour with 1 ml thionylchloride. The solution was reacted with a few drops of triethylamine, washed with water and concentrated by evaporation to dryness in a vacuum. The residue was dissolved in isopropanol and reacted with an ether solution of hydrogen chloride. There was obtained 7-chloro-1-methyl-2-chloromethyl-5-phenyl-2,3-dihydro-1H-1,4-benzodiazepine hydrochloride. The product was also identical with the product obtained in Example 10 of application Ser. No. 335,986; m.p. 110°–112° C.

EXAMPLE 12

200 mg of 3,8-dichloro-1-methyl-6-phenyl-1,2,3,4-tetrahydro-1,5-benzodiazocine hydrochloride were heated under reflux for 1 hour in 100 ml tetrachloroethane. The solvent was then distilled off in a vacuum and the residue was recrystallized from isopropanol. The product obtained was 7-chloro-1-methyl-2-chloromethyl-5-phenyl-2,3-dihydro-1H-1,4-benzodiazepine hydrochloride which was identical with the product in Example 11 hereinbefore; m.p. 110°–112° C.

In the same manner as illustrated in above Examples the following diazepine compositions shown in Table 2 were made. Many of these compounds are described also in our above-mentioned copending application Ser. No. 355,986.

TABLE 2

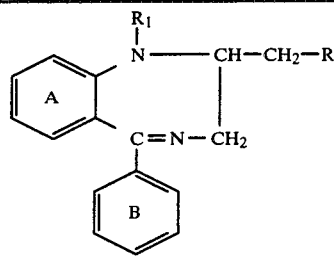

| Substitution in phenylring A | Substitution in phenylring B | R₁ | R | m.p. (°C.) |
|---|---|---|---|---|
| 7-Cl | H | CH₃ | OC₂H₅ | oil |
| 7-Cl | H | CH₃ | i-OC₃H₇ | oil |
| 7-Cl | H | CH₃ | C≡N | 210–214 (hydrochlorides) |
| 7-Cl | H | CH₃ | —N(CH₂CH₂)₂O (morpholino) | 237–245 (dihydrochloride) |
| H | H | CH₃ | Cl | 195–198 (hydrochloride) contains 0.65 mol isopropanol and ½ mol water |
| H | H | CH₃ | —N(CH₂CH₂)₂N—CH₃ (N-methylpiperazino) | oil |
| 7-Cl | 2-Cl | CH₃ | OH | 166–168 |
| 7-Cl | 2-F | CH₃ | Cl | 161–165 (hydrochloride) |
| 7-Cl | 2-F | CH₃ | OH | 173–175 |
| 7-Cl | 2,4-di-Cl | CH₃ | OH | 225 (hydrochloride) |
| 7-Br | H | CH₃ | Cl | 95–98 (hydrochloride) |
| 7-CH₃ | H | CH₃ | Cl | 130–133 (hydrochloride, contains 1 mol isopropanol) |
| 7-CH₃ | H | CH₃ | OH | 192–195 (hydrochloride) |
| 7-OCH₃ | H | CH₃ | Cl | 191–193 (hydrochloride) |
| 7-OCH₃ | H | CH₃ | OH | 186–189 (hydrochloride) |
| 7-Cl | 3,4-di-Cl | CH₃ | Cl | 139–141 (hydrochloride) |
| 7-Cl | 3-CF₃ | CH₃ | OH | 226–228 (hydrochloride) |
| 7-Cl | H | CH₃ | —N(CH₂CH₂)₂N—CH₃ (N-methylpiperazino) | 214–215 (trihydrochloride contains 1 mol ethanol) |
| 7-Cl | H | CH₃ | phthalimido | 151–152 |
| 7-Cl | H | CH₃ |  | 206–209 (dihydrochloride contains 0.5 mol isopropanol) |

TABLE 2-continued

| Substitution in phenylring A | Substitution in phenylring B | R₁ | R | m.p. (°C.) |
|---|---|---|---|---|
| 7-Cl | H | CH₃ | —O—C(=O)—C₆H₅ | 175 (after sintering from 160) (hydrochloride) |
| 7-Cl | H | CH₃ | Br | oil |
| 7-Cl | H | CH₃ | —S—C₆H₅ | 185–187 (hydrochloride) |
| 7-Cl | H | —CH₂—C₆H₅ | OH | 208 (decomposed) (hydrochloride) |
| 7-Cl | 2-CF₃ | CH₃ | OH | 196–201 (hydrochloride) |
| 7-Cl | 2-Cl | CH₃ | CN | 171–174° C. (hydrochloride) |
| 7-Cl | 2-Cl | CH₃ | O—CH(CH₃)₂ | 193–196° C. (hydrochloride) |
| 7-NO₂ | H | H | Cl | 148–149° C. |
| 9-NO₂ | H | H | Cl | 123–125° C. |
| H | 2-Cl | CH₃ | Cl | 198–200° C. (hydrochloride) |
| 7-Cl | H | CH₂CH₂Cl | Cl | 114–116° C. |
| 7-Cl | H | C₂H₅ | OH | 196–202° C. (hydrochloride) |
| 7,8-di-OCH₃ | 3,4-di-OCH₃ | CH₃ | OH | 111–115° C. (hydrochloride) |
| 7-CH₃S | H | CH₃ | Cl | oil |
| 7-Br | H | CH₃ | OH | 241–242° C. (hydrochloride) |
| 7-F | H | CH₃ | OH | 99–101° C. (hydrochloride + 1 mol. isopropanol) |
| 7,8-O—CH₂—CH₂—O— | 3,4-di-OCH₃ | CH₃ | Cl | 173–176° C. |
| 7-CH₃S | H | CH₃ | OH | 213–216° C. (hydrochloride) |
| 7-Cl | 2,6-di-Cl | CH₃ | OH | 218–220° C. (hydrochloride) |
| 7-Cl | 2,3-di-Cl | CH₃ | OH | 226–228° C. (hydrochloride) |
| 7-Cl | 3,4-di-Cl | CH₃ | OH | 242–245° C. (hydrochloride) |
| 7-Cl | 2-CH₃ | CH₃ | OH | 186–189° C. (hydrochloride) |
| 7-Cl | 2-Br | CH₃ | OH | 205–206° C. (hydrochloride) |
| H | 2-Cl | CH₃ | OH | 133–134° C. |
| 7-Cl | 2-Cl | CH₃ | OCH₃ | 192–194° C. (hydrochloride) |
| 7-Cl | 2-Cl | CH₃ | Cl | 176–178° C. (hydrochloride) |
| 7-Cl | 2-Cl | CH₃ | OC₂H₅ | 158–161° C. (hydrochloride) |

TABLE 2-continued

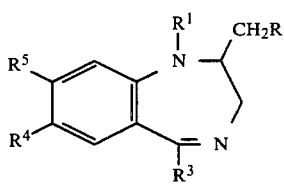

| Substitution in phenylring A | Substitution in phenylring B | $R_1$ | R | m.p. (°C.) |
|---|---|---|---|---|
| 7-Cl | H | $CH_3$ | O—⌬ | 180° C. (hydrochloride) |
| 7-Cl | H | $CH_3$ | O—⌬—Cl | 192–200° C. (hydrochloride) |
| 7-Cl | H | $CH_3$ | $NHCH_2$—⌬ | 165–168° C. (dihydrochloride) |

We claim:

1. A process of making benzodiazepine derivatives of the formula

wherein
R represents halogen, hydroxy, lower alkoxy or an amino group corresponding to the formula $$-N\begin{matrix}R^6\\R^7\end{matrix}$$

wherein $R^6$ and $R^7$ may be the same or different and are selected from hydrogen, lower alkyl or benzyl, or $R^6$ and $R^7$ together form a piperidino group;
$R^1$ represents hydrogen or lower alkyl;
$R^3$ represents phenyl or phenyl substituted at least once with a group selected from halogen, nitro, trifluoromethyl, lower alkyl and lower alkoxy;
$R^4$ represents hydrogen, halogen, nitro, trifluoromethyl, lower alkyl or lower alkoxy; and
$R^5$ is hydrogen, or a pharmaceutically acceptable acid addition salt thereof, said process comprising subjecting a benzodiazocine corresponding to the formula

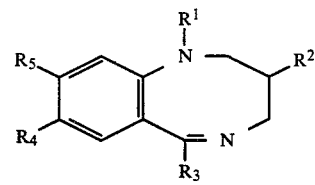

or an acid addition salt thereof wherein $R^1$, $R^3$, $R^4$ and $R^5$ have the same meanings as above and $R^2$ represents (i) halogen or (ii) hydroxy, in the case of (i) to thermal treatment in an inert solvent in the presence of a nucleophilic agent which produces a hydroxy, lower alkoxy or amino residue

wherein $R^6$ and $R^7$ have the same meanings as above, or in the case of (ii) to thermal treatment with a halogenating Lewis acid in a solvent.

2. A process according to claim 1 wherein the thermal treatment is effected at about the reflux temperature of the solvent.

3. A process of making benzodiazepine derivatives of the formula

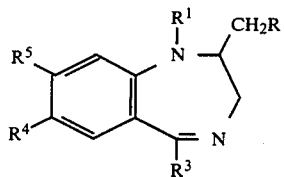

wherein
R represents halogen, hydroxy, lower alkoxy, or an amino group corresponding to the formula

wherein $R^6$ and $R^7$ together form a piperidino group;
$R^1$ represents hydrogen or lower alkyl;
$R^3$ represents phenyl or phenyl substituted at least once with a group selected from halogen, nitro, trifluoromethyl, lower alkyl, and lower alkoxy;
$R^4$ represents hydrogen, halogen, nitro, trifluoromethyl, lower alkyl or lower alkoxy; and
$R^5$ represents hydrogen,
or a pharmaceutically acceptable acid addition salt thereof, said process comprising subjecting a benzodiazocine corresponding to the formula

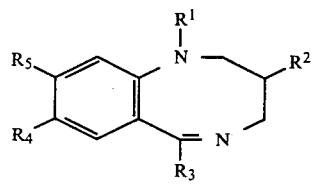

or an acid addition salt thereof wherein $R^1$, $R^3$, $R^4$ and $R^5$ have the same meanings as above and $R^2$ represents (i) halogen, or (ii) hydroxy, in the case of (i) to thermal treatment in an inert solvent or in the case of (i) to thermal treatment in an inert solvent in the presence of a nucleophilic agent which produces a hydroxy, lower alkoxy, or an amino residue

wherein $R^6$ and $R^7$ have the same meaning as above, or in the case of (ii) to thermal treatment with thionyl chloride in an inert solvent,
whereby the benzodiazocine compound undergoes rearrangement and ring contraction.

4. A process according to claim 3, wherein $R^1$ represents lower alkyl.

5. A process according to claim 4, wherein R represents chlorine.

6. A process according to claim 4, wherein R represents hydroxy.

7. A process according to claim 4, wherein R represents methoxy.

8. A process according to claim 4, wherein R represents piperidino.

9. A process according to claim 7, wherein the thermal treatment is affected at about the reflux temperature of the solvent.

10. A process of making benzodiazepine derivatives of the formula

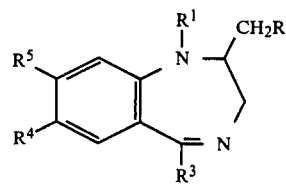

wherein
R represents halogen, hydroxy, lower alkoxy or an amino group corresponding to the formula

wherein $R^6$ and $R^7$ together form a piperidino group;
$R^1$ represents lower alkyl;
$R^3$ represents phenyl or phenyl substituted at least once with halogen;
$R^4$ represents hydrogen or halogen; and
$R^5$ represents hydrogen, or a pharmaceutically acceptable acid addition salt thereof, said process comprising subjecting a benzodiazocine compound corresponding to the formula

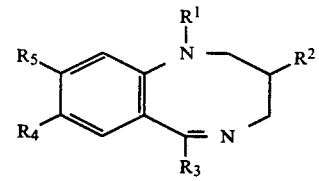

or an acid addition salt thereof wherein $R^1$, $R^3$, $R^4$ and $R^5$ have the same meanings as above and $R^2$ represents (i) halogen or (ii) hydroxy, in the case of (i) to thermal treatment in an inert solvent, or in the case of (i) to thermal treatment in an inert solvent in the presence of a nucleophilic agent which produces a hydroxy, lower alkoxy or amino residue

wherein $R^6$ and $R^7$ have the same meaning as above, or in the case of (ii) to thermal treatment with a halogenating Lewis acid in a solvent,
whereby the benzodiazocine compound undergoes rearrangement and ring contraction.

11. A process according to claim 10, wherein the thermal treatment is effected at about the reflux temperature of the solvent.

12. A process according to claim 10, wherein said halogenating Lewis acid is thionyl chloride.

13. A process according to claim 10, wherein R represents halogen, hydroxy or lower alkoxy.

14. A process according to claim 1, wherein $R^4$ represents hydrogen or halogen.

15. A process according to claim 1, wherein in the formula

$R^6$ and $R^7$ may be the same or different and are selected from hydrogen, lower alkyl, or $R^6$ and $R^7$ together form a piperidino group.

16. A process for the production of 7-chloro-1-methyl-2-hydroxymethyl-5-phenyl-2,3-dihydro-1H-1,4-benzodiazepine as defined in claim 12, which comprises heating 3,8-dichloro-1-methyl-6-phenyl-1,2,3,4-tetrahydro-1,5-benzodiazocine hydrochloride in an inert solvent containing sodium hydroxide at an elevated temperature.

17. A process for the production of 7-chloro-1-methyl-2-methoxymethyl-5-phenyl-2,3-dihydro-1H-1,4-benzodiazepine as defined in claim 12 which comprises heating 3,8-dichloro-1-methyl-6-phenyl-1,2,3,4-tetrahydro-1,5-benzodiazocine hydrochloride together with a solution of sodium metal in methanol at an elevated temperature.

18. A process for the production of 7-chloro-1-methyl-2-piperidinomethyl-5-phenyl-2,3-dihydro-1H-1,4-benzodiazepine as defined in claim 12 which comprises heating 3,8-dichloro-1-methyl-6-phenyl-1,2,3,4-tetrahydro-1,5-benzodiazocine hydrochloride together with piperidine at an elevated temperature.

19. A process for the production of 7-chloro-1-methyl-2-chloromethyl-5-phenyl-2,3-dihydro-1H-1,4-benzodiazepine as defined in claim 12 which comprises heating a solution of thionyl chloride and 8-chloro-1-methyl-3-hydroxy-6-phenyl-1,2,3,4-tetrahydro-1,5-benzodiazocine in benzene at an elevated temperature.

20. A process for the production of 7-chloro-1-methyl-2-chloromethyl-5-phenyl-2,3-dihydro-1H-1,4-benzodiazepine as defined in claim 12 which comprises heating 3,8-dichloro-1-methyl-6-phenyl-1,2,3,4-tetrahydro-1,5-benzodiazocine in tetrachloroethane at an elevated temperature.

* * * * *

UNITED STATES PATENT AND TRADEMARK OFFICE
CERTIFICATE OF CORRECTION

PATENT NO. : 4,595,531

DATED : June 17, 1986

INVENTOR(S) : Wolfgang MILKOWSKI et al.

It is certified that error appears in the above-identified patent and that said Letters Patent is hereby corrected as shown below:

IN THE TITLE PAGE:

Item [63], "359,989" should read --355,989--;

Item [30], "2215583" should read --22 21 558 --.

Signed and Sealed this

Fourteenth Day of October, 1986

[SEAL]

Attest:

DONALD J. QUIGG

Attesting Officer

Commissioner of Patents and Trademarks